US009863826B2

United States Patent
Xu et al.

(10) Patent No.: US 9,863,826 B2
(45) Date of Patent: Jan. 9, 2018

(54) SENSOR DEVICE AND RESIDUAL STRESS DETECTION SYSTEM EMPLOYING SAME

(71) Applicant: BEIJING INSTITUTE OF TECHNOLOGY, Beijing (CN)

(72) Inventors: Chunguang Xu, Beijing (CN); Lang Xu, Beijing (CN); Qinxue Pan, Beijing (CN); Dingguo Xiao, Beijing (CN); Xiao Li, Beijing (CN); Jun Guo, Beijing (CN); Wentao Song, Beijing (CN); Haiyang Liu, Beijing (CN)

(73) Assignee: BEIJING INSTITUTE OF TECHNOLOGY, Beijing (CN)

( * ) Notice: Subject to any disclaimer, the term of this patent is extended or adjusted under 35 U.S.C. 154(b) by 188 days.

(21) Appl. No.: 14/648,225

(22) PCT Filed: Jul. 2, 2013

(86) PCT No.: PCT/CN2013/078687
§ 371 (c)(1),
(2) Date: May 28, 2015

(87) PCT Pub. No.: WO2014/082446
PCT Pub. Date: Jun. 5, 2014

(65) Prior Publication Data
US 2015/0300897 A1 Oct. 22, 2015

(30) Foreign Application Priority Data
Nov. 29, 2012 (CN) .......................... 2012 1 0500278

(51) Int. Cl.
*G01N 29/04* (2006.01)
*G01N 29/07* (2006.01)
(Continued)

(52) U.S. Cl.
CPC .............. *G01L 1/255* (2013.01); *G01N 29/04* (2013.01); *G01N 29/041* (2013.01); *G01N 29/07* (2013.01);
(Continued)

(58) Field of Classification Search
CPC .. G01L 1/255; G01N 29/041; G01N 29/2487; G01N 29/07; G01N 29/265;
(Continued)

(56) References Cited

U.S. PATENT DOCUMENTS 4,170,145 A 10/1979 Kennedy et al.
4,712,428 A * 12/1987 Ishii ................... G01N 29/2487
73/644

(Continued)

FOREIGN PATENT DOCUMENTS

CN 101261249 9/2008
CN 201210151 3/2009
(Continued)

OTHER PUBLICATIONS

International Search Report for PCT/CN2013/078687 dated Oct. 17, 2013.
(Continued)

*Primary Examiner* — J M Saint Surin
(74) *Attorney, Agent, or Firm* — Ladas & Parry, LLP

(57) ABSTRACT

A sensor device, comprising two symmetrically disposed sonolucent wedges (5), and a connecting piece for fixedly connecting the two sonolucent wedges (5); the upper surfaces of the sonolucent wedges (5) are provided with inclined planes; installation holes are formed on the inclined planes; transducers (3) are installed in respective installation holes; one transducer (3) is used to generate ultrasonic waves, and the other transducer (3) is used to receive the ultrasonic waves generated by the previous transducer (3).
(Continued)

The residual stress detection system comprises a sensor device, an ultrasonic transmission card, and a data acquisition card.

13 Claims, 6 Drawing Sheets

(51) Int. Cl.
- G01N 29/24 (2006.01)
- G01N 29/30 (2006.01)
- G01N 29/44 (2006.01)
- G01N 29/265 (2006.01)
- G01L 1/25 (2006.01)

(52) U.S. Cl.
CPC ....... *G01N 29/2487* (2013.01); *G01N 29/265* (2013.01); *G01N 29/30* (2013.01); *G01N 29/44* (2013.01); *G01N 29/4472* (2013.01); *G01N 2291/0289* (2013.01); *G01N 2291/02827* (2013.01); *G01N 2291/0421* (2013.01); *G01N 2291/0425* (2013.01); *G01N 2291/102* (2013.01)

(58) Field of Classification Search
CPC .... G01N 29/4472; G01N 29/04; G01N 29/44; G01N 29/30; G01N 2291/102; G01N 2291/0421; G01N 2291/0425; G01N 2291/02827; G01N 2291/0289
USPC .......................................................... 73/597
See application file for complete search history.

(56) References Cited

U.S. PATENT DOCUMENTS

| | | | | |
|---|---|---|---|---|
| 5,094,108 A | * | 3/1992 | Kim | G01N 29/041 310/335 |
| 5,172,591 A | | 12/1992 | Bohon | |
| 5,359,207 A | * | 10/1994 | Turner | H01L 27/14643 250/208.1 |
| 7,938,007 B2 | * | 5/2011 | Huebler | G01N 29/07 73/622 |
| 9,134,280 B2 | * | 9/2015 | Cataldo | G01N 29/043 |
| 2007/0000328 A1 | * | 1/2007 | Buttram | G01H 5/00 73/597 |
| 2008/0127732 A1 | * | 6/2008 | Owens | G01N 29/043 73/632 |
| 2009/0064787 A1 | * | 3/2009 | Kennedy | G01N 29/265 73/634 |
| 2013/0218490 A1 | * | 8/2013 | Poirier | G01N 29/069 702/56 |

FOREIGN PATENT DOCUMENTS

| | | | |
|---|---|---|---|
| CN | 101571513 | | 11/2009 |
| CN | 201803990 | * | 4/2011 |
| CN | 102393266 | | 3/2012 |
| CN | 102662004 A | * | 9/2012 |
| CN | 102721746 | * | 10/2012 |
| CN | 103017952 | | 4/2013 |
| CN | 103017953 | | 4/2013 |
| CN | 103018325 | | 4/2013 |
| CN | 103018326 | | 4/2013 |
| JP | 55043487 | * | 3/1980 |
| JP | 59-191665 | | 12/1984 |
| JP | 60097226 | * | 5/1985 |
| JP | 61-21961 | | 2/1986 |

OTHER PUBLICATIONS

Written Opinion of the International Search Authority for PCT/CN2013/078687, dated Oct. 17, 2013, and its English translation from WIPO.

International Preliminary Report on Patentability Chapter I for PCT/CN2013/078687, dated Jun. 2, 2015, and its English translation from WIPO.

Office Action dated Jun. 20, 2017 for Japanese Patent Application No. 2016-188006 and its English machine translation provided by Applicant's foreign council.

* cited by examiner

SENSOR DEVICE AND RESIDUAL STRESS DETECTION SYSTEM EMPLOYING SAME

CROSS-REFERENCE TO RELATED APPLICATION(S)

This application is the U.S. National Stage of International Patent Application No. PCT/CN2013/078687, filed on Jul. 2, 2013, which claims the priority of Chinese Patent Application No. 201210500278.6, filed on Nov. 29, 2012 with the Chinese Intellectual Property Office the disclosures of which are hereby incorporated in their entireties by reference.

FIELD OF THE INVENTION

The presented invention relates to a sensor device and residual stress detection system employing same. The residual stress at certain depth from the surface of metal materials can be detected by employment of ultrasonic longitudinal waves in the presented invention.

BACKGROUND OF THE INVENTION

The available techniques for the measurement of residual stress mainly include hole drilling and X-Ray diffraction. The measurement by hole drilling provides a higher accuracy, which is premised on damaged surface status of materials. The surface needs to be prepared by polishing treatment before the measurement, producing residual stress undoubtedly. Also the process of sticking strain gages is time-consuming so that a real-time detection cannot be achieved. X-Ray diffraction is mainly applied in non-destructive measurement. It is not possible to realize an on-site measurement with X-Ray diffraction due to its harmful radiation to human body, as well as long testing time, even though it has been put on the market.

Although many studies have been carried out on stress measurement by using ultrasound, it cannot meet the requirement of on-site measurement due to unreasonable design of structure, various interfering factors, and poor repeatability. The critically refracted longitudinal ($L_{CR}$) wave, which propagates along the surface of the specimen, is not sensitive to the roughness of the surface. Therefore there is no need to conduct special treatments to the surface, and it is capable of measuring the average value of stress value at a depth of about one wavelength from a surface based on a simple principle of measurement.

SUMMARY OF THE INVENTION

In view of the above problems, an object of the present invention is to provide a sensor device and residual stress detection system which is insensitive to surface roughness and needs no special treatment to the surface.

The present invention provides a sensor device, comprising two symmetrically disposed sonolucent wedges, and a connecting piece for fixedly connecting the two sonolucent wedges; the upper surfaces of the sonolucent wedges are provided with inclined planes; installation holes are formed on the inclined planes; transducers are installed in respective installation holes, in which one transducer is used to generate ultrasonic waves, and the other transducer is used to receive the ultrasonic waves generated by the previous transducer.

The present invention can realize the function of fast and accurately determining the value of residual stress, as well as rapid and reliable operation.

Circular bosses projecting downward are preferably formed at the bottom of the plexiglass wedges.

This can reduce the contact area between the wedges and the plate as well as errors caused by plate deformation without affecting the energy of ultrasound beams.

The lower surface of the circular bosses preferably has the same curvature with the surface of the metal material to be measured.

In this way the residual stress can be detected by using this pair of curved surface, especially for the outer and inner surface of the pipe.

A cavity is preferably formed between the aperture wall of the installation hole and the transducer, in which a coupling agent is sealed.

The accuracy of detection can be provided by sealing the coupling agent.

A small hole used for oiling into the cavity is preferably perforated in the side wall of the plexiglass wedge.

In a case that the fuel is low, oiling into the cavity can be made by a syringe through the small hole, without removing the sensor.

The present invention further provides a residual stress detection system, comprising a sensor device as described in the first technical solution, an ultrasonic transmission card, and a data acquisition card; the ultrasonic waves generated by the ultrasonic transmission card is received by the sensor device and then collected by the data acquisition card.

The high frequency date acquisition card with its acquisition frequency of 1 GHz is employed since the stress-induced change of ultrasonic transit time is in nanoseconds. In addition, the ultrasonic transmission card is integrated with the date acquisition card, resulting in a system with a higher degree of integration and enhanced reliability, as well as a more portable industrial personal computer (IPC) with significantly reduced size.

Preferably a temperature acquisition card is further provided to acquire real-time ambient temperature and eliminate the measurement error of stress due to change of ambient temperature.

Therefore the system can be adapted for measurement under a complex environment so as to have a wider range of applications.

Figure 1:
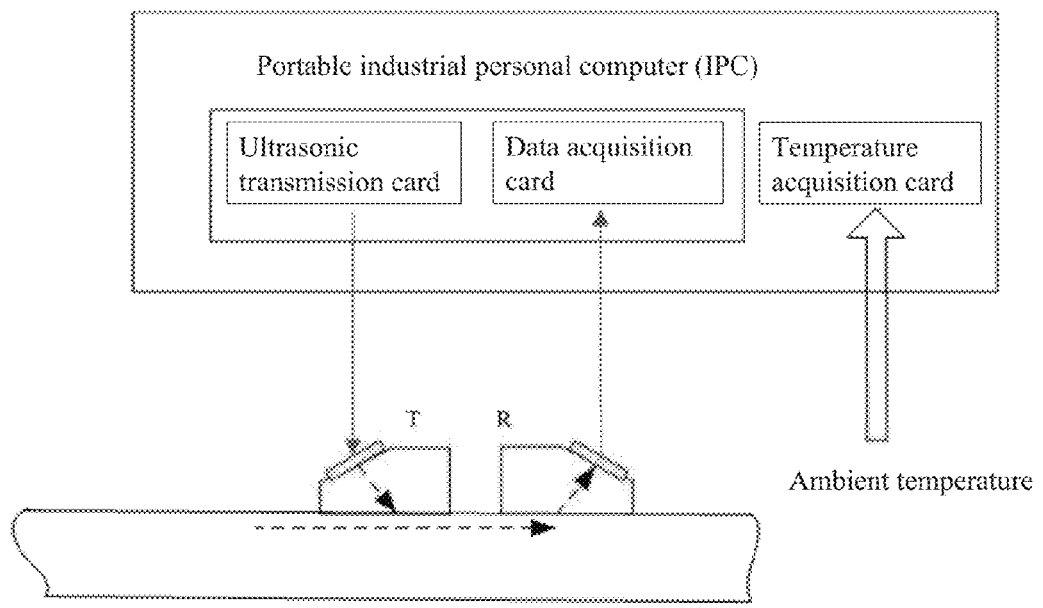
FIG. 1 is a schematic diagram of hardware structure of the detection device.

ILLUSTRATION OF LABEL NUMBERS 1, end fixed plate; 2, top fixed plate; 3, transducer; 4, fixed plate; 5, plexiglass wedge (sonolucent wedge); 6, magnetic base switch; 7, magnetic base; 8, sidewall oiling hole; 9, cylindrical cavity; 10, aluminum block; 11, magnetic steel block; 12, magnet; 14, columns; 15, fixed block; 16, stepping motor; 17, welding steel; 18, fixing device; 19, slider; 20, linear rail; 21, flexible strut; 22, linear welding; 23, sensor device; 24, link block; 25, sleeve; 26, spring; 27, baffle; 28, circular boss; 29, support piece.

DESCRIPTION OF THE EMBODIMENTS

The preferred embodiments of the present invention will be described in details as follows. In the following respective preferred embodiments, same numerals represent same component respectively.

In different embodiments, the shapes, structures, etc. corresponding to the same component have not been drawn in the completely same scale since the figures are schematic views, and there are certain difference. All structures shown in the drawing figures are suitable for use in the preferred embodiments in the present invention in a case of non-special explanation. In addition, the description of the structure is omitted in a case where the structure is as same as the structure described in the previous embodiment.

When an ultrasonic longitudinal wave is incident at the first critical angle, it will stimulate in the specimen surface the $L_{CR}$ wave. The velocity change of the $L_{CR}$ wave and the stress change satisfy the acousto-elasticity equation. By precisely measuring the velocity change of sound, it can reflect the value and direction of stress in measuring region.

Embodiment 1

The near-surface residual stress detection system for metal materials, includes two major parts, that are hardware and software, and auxiliary equipment. As shown in FIG. 1, based on a computer platform, the present invention mainly comprises several parts, such as an exciting and receiving probe, an ultrasonic transmittance card, a data acquisition card, a computer system, a transmission line, etc. When there is a large temperature difference, the plexiglass wedge 5 (sonolucent wedge) and top fixed plate 2 would experience deformation caused by thermal expansion and contraction. A temperature acquisition card is further installed to acquire real-time ambient temperature by software (shown by the hollow arrow in FIG. 1), and eliminate the deformation of mechanical part of the system and effect on sound speed both caused by change of ambient temperature, so that the system can be adapted for measurement under a complex environment and have a wider range of applications. The high frequency date acquisition card with its acquisition frequency of 1 GHz is employed since the stress-induced change of ultrasonic transit time is in nanoseconds. In addition, the ultrasonic transmission card is integrated with the date acquisition card, resulting in a system with a higher degree of integration and enhanced reliability, as well as a more portable industrial personal computer (IPC) with significantly reduced external dimensions.

Figure 2:
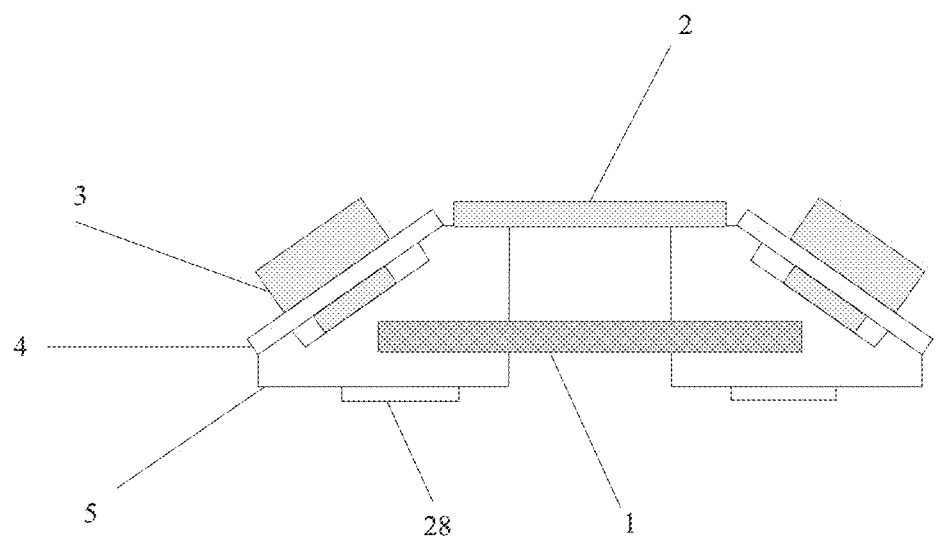
FIG. 2 is a schematic diagram of the near-surface residual stress detection system for metal materials.

In FIG. 1, the arrows indicate the transmission path of ultrasonic waves starting from the ultrasonic transmittance card, then to the sensor device, and then to the data acquisition card. FIG. 2 is a schematic diagram of the sensor (for pitch-catch of ultrasound) of residual stress detection system. In the actual measurement, slight deformation of the plate, would cause poor coupling in the deformation zone, and large ultrasonic transit time error during measurement. In the propagation direction of ultrasound beams, a circular boss 28 is machined at the bottom of the plexiglass wedge 5, with a slightly larger area than projection area of the sound beam at the bottom, which may reduce the contact area of the wedge and the plate without affecting the energy of ultrasonic beams, and reduce the error caused by deformation of the plate. The axis of the circular boss 28 can preferably intersect with the axis of the transducer 3 (for pitch-catch of ultrasound). Instead of the circular boss 28, bosses in other shapes can also be used.

As shown in FIG. 2, the transducers 3 are connected to the fixed plates 4 through threads, and the fixed plates 4 are fixed in the plexiglass wedges 5 through bolts; installation holes are formed on the inclined planes of the plexiglass wedges 5; transducers 3 are installed in the installation holes in the way perpendicular to the inclined planes; one of the two transducers 3 is used to generate ultrasonic waves (T), and the other is used to receive the ultrasonic waves (R). The bottom ends of transducers 3 are coupled with the plexiglass wedges 5 by a coupling agent. The coupling agent is a layer of sonolucent medium applied between the sensor device and the workpiece surface, such as glycerin, of which the main function is to exclude the air between the sensor device and the workpiece surface, so that ultrasonic waves can effectively pass through the workpiece, ensuring sufficient transmittance of sound intensity for the detected surface, and the purpose of measurement can be achieved. In addition, the coupling agent with certain fluidity may also reduce friction, and play a role in lubricating the movement of the sensor device on the workpiece during detection in direct contact mode.

Figure 3:
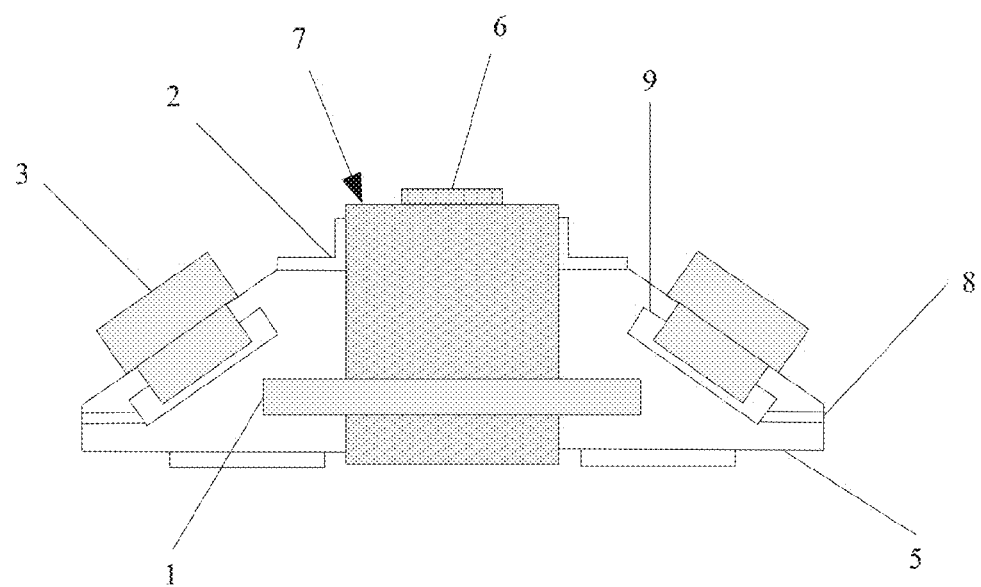
FIG. 3 is a schematic diagram of the magnetic ultrasonic oblique incident sensor device.
Figure 4:
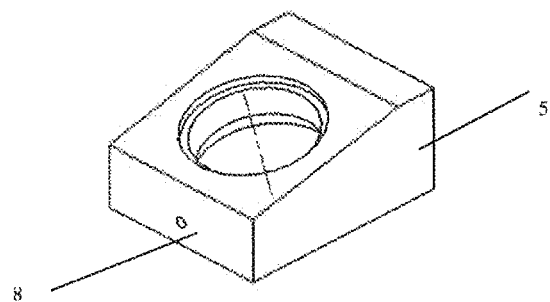
FIG. 4 is a three-dimensional diagram of plexiglass wedge.

Also as shown in FIG. 3, threads are processed in the inclined planes of the plexiglass wedges 5, so that the ultrasonic transducers 3 are threaddedly fixed with the plexiglass wedges 5. Wedge-shaped, as shown in FIG. 4, the plexiglass wedge 5, having a parallel top surface and bottom surface, wherein the connecting surfaces between the top and bottom surfaces are three vertical planes perpendicular to the top and bottom surfaces and one inclined plane. As shown in FIGS. 2 and 3, each of two sides of the wedge (the sides adjacent to the inclined plane) has one end fixed plate 1; two plexiglass wedges 5 are connected via the top fixed plate 2, and two inclined planes are oppositely disposed, so that the spacing of the whole device is kept constant based on these three fixed plates.

The ultrasonic transmittance card is controlled by the portable IPC to transmit electrical impulses, which then stimulates the ultrasonic transmitting transducers to emit the ultrasonic longitudinal waves, resulting in the $L_{CR}$ wave refracted on the specimen. After the ultrasonic signal received by the receiving transducer is received by the data acquisition card, a comprehensive analysis of the discrete signals from the data acquisition card and ambient temperature signals collected by temperature acquisition card would be conducted by the portable IPC computer, in order to obtain stress analysis results with a high degree of reliability.

The software part of the near-surface residual stress detection system for metal materials has been developed successfully by using VC++ to write running program, interpolation process and cross-correlation algorithm of the boards, in order to set a calibration device. During the detection of the residual stress of the curved surface, the calibration device is set up to calibrate the incident angles of ultrasonic waves after simulating the curved surface with three-dimensional software, so that the strongest waveform of excited $L_{CR}$ wave can be achieved. By controlling the excitation and reception of ultrasonic signals as well as signal processing, analyzing and storing with software, it can realize fast and accurate determination of the value of residual stress, as well as rapid and reliable operation.

The advantage of the present invention is that drawing up the software by using VC++, of which the main function is to control the excitation and reception of ultrasonic signals as well as signal processing, analyzing and storing, enabling simplified and intuitive man-machine interface operation, and rapid non-destructive on-site detection of stress value, without any need of polishing treatment to the surface prior to the measurement.

The present invention provides the detection of residual stress at a certain depth from the surface of metal materials by using ultrasonic longitudinal waves. The certain depth (in mm) can be changed as follows by changing the frequency of the transducers (in MHz):

Frequencies: 1 MHz, 2.5 MHz, 5 MHz, 7.5 MHz, 10 MHz, 15 MHz.

When the material is steel, the depths corresponding to the frequencies are, respectively, 5.90 mm, 2.36 mm, 1.20 mm, 0.79 mm, 0.39 mm and 0.59 mm; when the material is aluminum, the corresponding depths are, respectively, 6.40 mm, 2.56 mm, 1.28 mm, 0.85 mm, 0.64 mm and 0.43 mm; when the material is copper, the corresponding depths are, respectively, 4.70 mm, 1.88 mm, 0.94 mm, 0.63 mm, 0.47 mm and 0.31 mm.

Embodiment 2

Sensor device 23 may also employ other configurations. For example, when domestic and foreign designers are designing the configuration of ultrasonic oblique incident sensor, it is common for them to fix the ultrasonic transducer in the plexiglass wedge with bolts or special fixture. While for this configuration, in a case where the transducer is coupled with the wedge, every time the transducer need to be removed and mounted again after coating with the coupling agent, resulting in an increased inconvenience.

In the present embodiment, as shown in FIG. 3, the sensor device comprises plexiglass wedges 5, a magnetic base 7 and fixed plates 4. Threads are processed in the inclined planes of the plexiglass wedges 5, so that the ultrasonic transducers 3 are threadedly fixed with the plexiglass wedges 5. Cylindrical cavities 9 are processed inside the plexiglass wedge 5, with diameters slightly larger (such as 4 mm larger) than that of the circular chips of the transducers 3. Therefore a sufficient amount of oil can be guaranteed and it will not have any effect on incidence of the ultrasonic waves even if there exit some certain air bubbles. The oiling holes 8 are processed in the side walls of the plexiglass wedges. When there is insufficient fuel, oiling into the cavities can be made by a syringe without removing the sensor. Same as in Embodiment 1, in order to reduce the contact area between plexiglass wedges 5 and the detected workpiece, a circular boss 28 is machined in the incident direction of the ultrasonic beam.

The accurate design of tilted angles of plexiglass wedges 5 is significantly critical for whether the $L_{CR}$ wave can be stimulated. The methods used in the design of tilted angles are as follows:
(1) First the cylindrical plexiglass sample with thickness of 20 mm is machined accurately. The accurate time difference of the bottom echo is calculated by using the pulse-echo method, so that the sound speed of plexiglass can be calculated.
(2) Then according to Snell's Law, which is defined as $$\frac{\sin\theta_0}{V_0} = \frac{\sin\theta_1}{V_1} \qquad (1)$$

Wherein, $\theta_0$ is the angle of the incident longitude wave measured from the normal of the boundary, $\theta_1$ is the angle of the refracted longitude wave measured from the normal of the boundary, $V_0$ is the velocity of the longitude wave in the plexiglass and $V_1$ is the velocity of the longitude wave in the detected metal. In order to stimulate the $L_{CR}$ wave, the calculation of the incident angle $\theta_0$ can be simplified as:

$$\theta_0 = \arcsin\left(\frac{V_0}{V_1}\right) \qquad (2)$$

The incident angle, $\theta_0$ is the designed tilted angle of plexiglass wedges 5. After calculation, the range of tilted angles necessary for different detected materials is shown as follows:

When the detected materials are, steel, aluminum or copper, the corresponding ranges of tilted angles are, 24°~27°, 22°~25°, 31°~34°, respectively.

Figure 5:
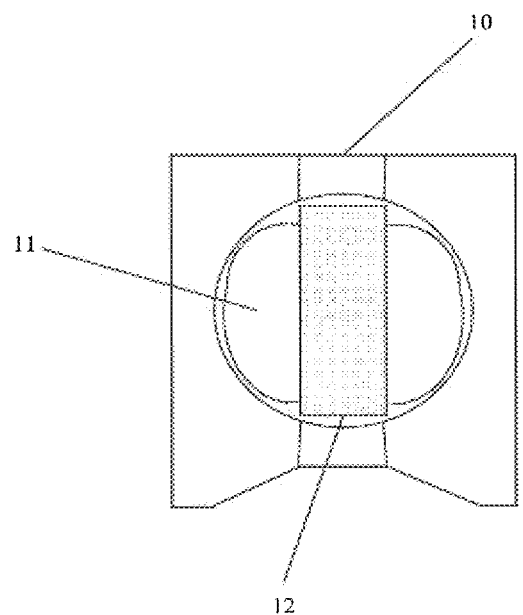
FIG. 5 is a schematic diagram of the strong magnetic base.

FIG. 5 is a schematic diagram of the strong magnetic base, including a magnetic base 7, a magnetic conductive steel block 11, a aluminum block 10 and a magnet 12. The magnetic base 7 with dimensions of 35 mm×30 mm×35 mm is selected, and the magnetic conductive steel block 11 is machined, and fitly assembled together with the magnet 12 (strong magnetic with thickness of 7 mm) inside the housing of the magnetic base 7. When the magnet 12 is rotated to a horizontal position by the magnetic base switch 6, the magnetic induction line is turned on and the magnetic base 7 provides external magnetic force; when the magnet 12 is rotated to a vertical position by the magnetic base switch 6 (as shown in FIG. 5), the magnetic induction line is turned off due to magnetic insulation effect of aluminum materials and the magnetic base 7 provides no external magnetic force, then the plexiglass wedges can be removed easily. The bottom of magnetic base 7 is slightly higher (such as 0.5 mm higher) than that of the circular bosses 28 of the plexiglass wedges 5, in order to ensure an good contact between the circular bosses 28 of the plexiglass wedges 5 and the detected piece.

If the width of the magnetic base 7 is not identical to that of the plexiglass wedges 5, the plexiglass wedges 5 may roll over when in use due to the resulted unevenly distributed magnetic force. Therefore in order to ensure that the magnetic force generated by the magnetic base 7 is applied uniformly on the contact surface between the plexiglass wedges 5 and the detected material, it is possible to mill a certain thickness (such as 2 mm) for the extra portion of the width of the magnetic base 7.

The plexiglass wedge 5, the magnetic base 7 and the end fixed plate 1 are connected through bolts, and the fixed plates 4 are installed on both sides of each plexiglass wedge 5. The upper surface of each plexiglass wedge 5 is connected to the magnetic base 7 by the top fixed plate 2, which is processed from for example, 3 mm-thick stainless steel to ensure the structural rigidity.

When in use, the coupling agent shall be coated on the bottom of the plexiglass wedges 5, and the sensor device 23 is places on the surface of the detected workpiece. The magnetic base switch 6 is rotated so that the device is firmly adsorbed on the workpiece by the strong magnetic force produced by the magnetic base 7. If there is a need to measure another point, the sensor device 23 can be easily removed by rotating the magnetic base switch 6 by 90 degrees, and then moved to another point for measurement.

Embodiment 3

Currently the measurement of residual stress by applying ultrasonic waves is mostly carried out for flat plates, while pipes can be seen everywhere in daily life. When the residual stress present in the inner or outer surface of the pipes is too large, a serious accident may be caused. Therefore, the stress detection of pipes has attracted more and more attention. When measuring the surface residual stress of curved surfaces such as pipes, an appropriate adjustment shall be made to the structure of the detected system.

When measuring the residual stress of the inner or outer surface of a pipe, the bottom of each plexiglass wedge 5 is machined, so as to have the same curvature as that of the pipe. Alternatively, a bottom surface contacting member with the same curvature of the pipe is mounted on the bottom surface of each plexiglass wedge 5. In addition, the magnetic base 7 can be mounted between two plexiglass wedges 5, providing a greater magnetic force to allow the coupling between wedges 5 and the pipe.

During the measurement, the position of the detection system is adjusted so that the line connecting two corresponding points of sensors is parallel to the pipe bus.

Figure 6:
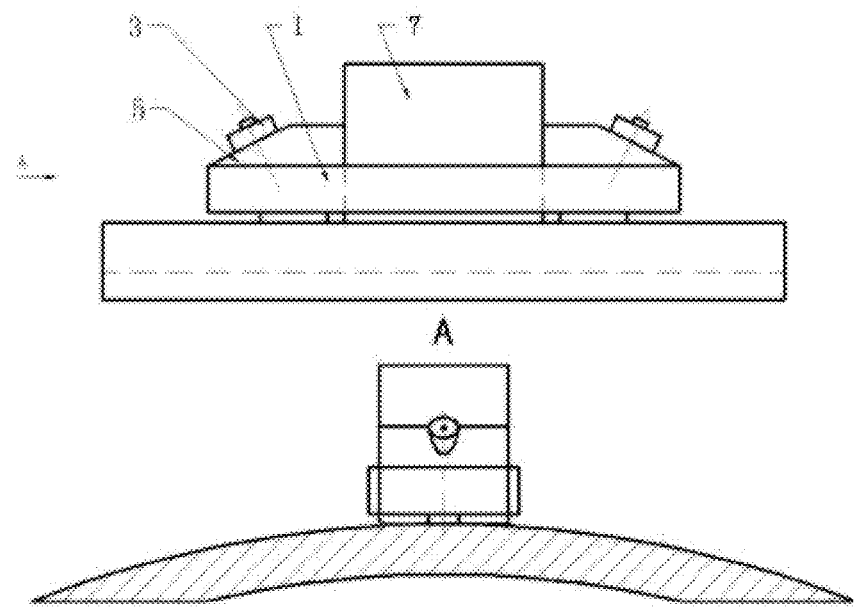
FIG. 6 is a schematic diagram of the outer-surface stress detection device for a pipe.

FIG. 6 is a schematic diagram of the outer-surface stress detection device for a pipe, including the plexiglass wedges 5, the ultrasonic transducers 3, the end fixed plate 1 and the magnetic base 7.

Figure 7:
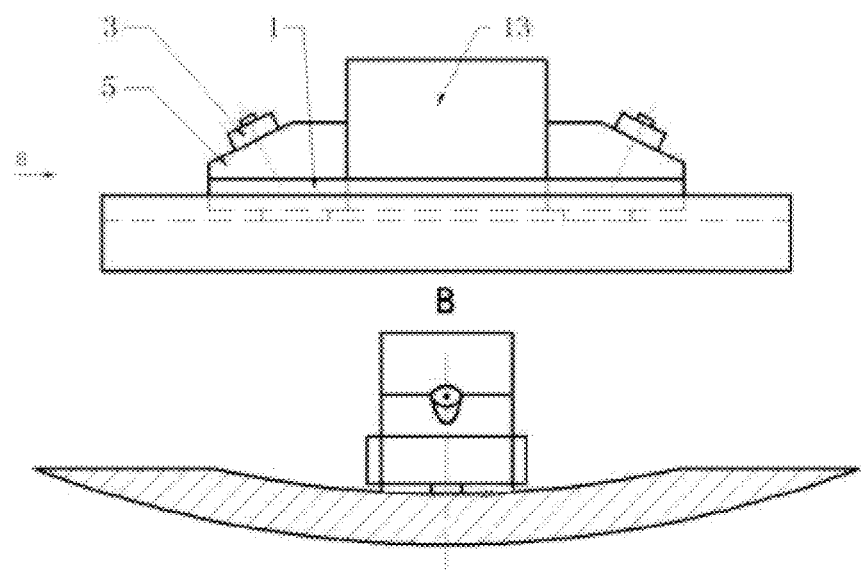
FIG. 7 is a schematic diagram of the inner-surface stress detection device for a pipe.

FIG. 7 is a schematic diagram of the inner-surface stress detection device for a pipe. The inner-surface stress detection for a pipe is more complicated than the outer-surface stress detection for a pipe, and it is very difficult to stimulate the $L_{CR}$ wave on the inner wall of the pipe, especially for a pipe with a greater curvature of its inner diameter. Because the normal magnetic base with dimensions of 35 mm×30 mm×335 mm comes in a relative large volume, machining of the magnetic base is needed to ensure that the outer walls of the end fixed plate 1 and wedges 5 will not interfere with the outer diameter of the pipe, and the result of the measurement is reliable.

When the residual stress of the plate-like component is detected, the direction of the normal is perpendicular to the plane of the plate, and all the ultrasonic beams emitted by the chip have the same incident angle. The $L_{CR}$ wave can be refracted when the wedges are machined with theoretical incident angle. While the normal of the pipe is perpendicular to the surface of the pipe, pointing towards the center, when the ultrasonic beams excited from the chip strike on the interface of the wedges and the pipe, the beams at different positions have different incident angles. When designing the wedges used for detecting the residual stress of the pipe surface, since the range of the excited angles is narrow for the $L_{CR}$ wave, it is usually necessary to calibrate the theoretical incident angles $\theta_{cr}$ with three-dimensional software, most preferably to ensure the incident angles of the excited ultrasonic beams closest to the edge of the ultrasonic transducer within the range of ≈, so that the $L_{CR}$ wave of the curved surface can be excited.

Embodiment 4

The ultrasonic non-destructive detection of residual stress and surface defects is mainly carried out in hand-held detection mode at home and aboard. The detection device from Embodiment 4 can allow automatic scanning detection.

Figure 8:
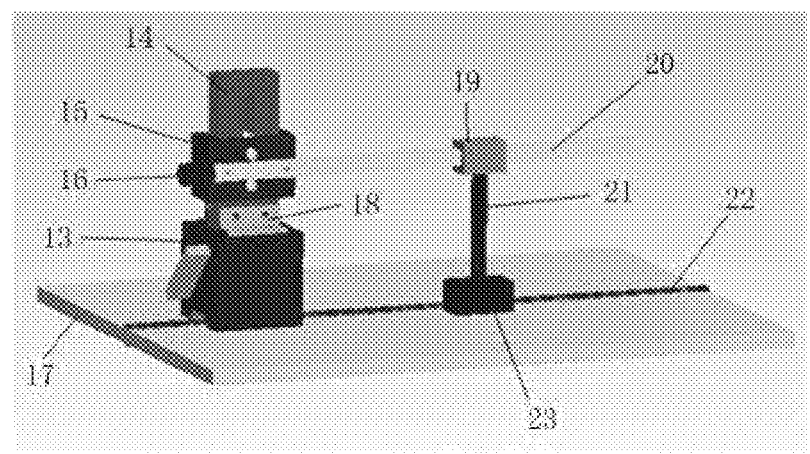
FIG. 8 is a schematic diagram of linear automatic scanning device for contact ultrasonic non-destructive detection.

As shown in FIG. 8, the linear automatic scanning device for contact ultrasonic non-destructive detection consists of several important parts such as a magnetic base 7, a stepping motor (including an optical encoder) 16, a slider 19, a linear rail 20, a flexible strut 21, a sensor device 23 and the like.

Magnetic attraction force of the magnetic base 7 is large enough and can be switched on and off through a knob. The bottom of the magnetic base 7 can be processed into a curved shape with same curvature based on the surface curvature of the detected workpiece, so that the magnetic base 7 and the detected workpiece fit closely, and the detection system becomes more stable. As a driven device, the stepping motor 16 actuates the slider 19 on the linear rail 20 to drive the sensor device 23 to perform automatic scanning. The position information of scanning is recorded and responded by a photoelectric encoder. The flexible strut 21 provides constant pressure for the detection sensor, enabling a good coupling between the sensor device 23 and the surface of the detected workpiece, as well as reliability and accuracy of the result.

Figure 9:
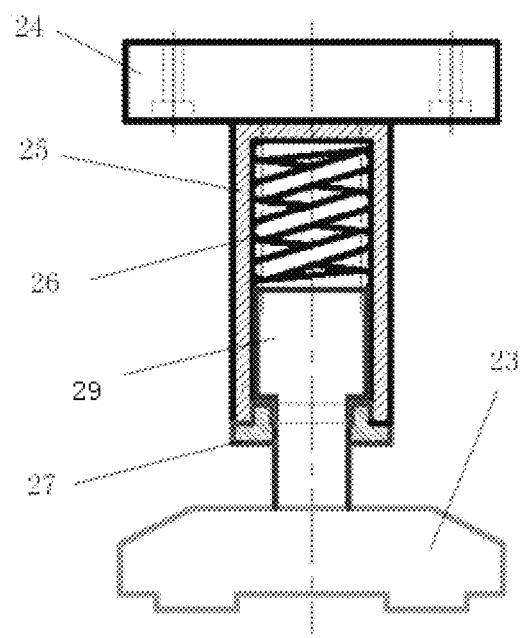
FIG. 9 is a local schematic diagram of the flexible strut.

As shown in FIG. 9, the flexible strut 21 mainly consists of several parts including a sleeve 25, a spring 26, a baffle 27, and a support piece 29 and the like. The spring 26 provides a pressing force to the flexible strut 21, enabling the sensor device 23 and the detected workpiece fit tightly. Even if rough and uneven surfaces occur during the measurement, the sensor device 23 can still be coupled with the detected surface well under the pressure.

As a driven part, the stepping motor 16 controls the scanning speed by adjusting its running speed. The position information of scanning is recorded and responded by a photoelectric encoder. It is possible to enable triggering by positions and enhance precision of scanning; the precision of grating scale is at least 0.1 mm. In order to reduce the mass of the detection device 23, aluminium alloy is selected to be the material for producing the linear rail 20, which has a size of about 40 mm×20 mm×500 mm. The slider 19 is connected by a flexible strut 21 to the sensor device 23. Working in pitch-catch mode, the sensor device 23 can be either a residual stress detection sensor, or surface defect detection sensor, or TOFD detection sensor.

An appropriate sensor device 23 selected based on the detection requirement is mounted on a flexible strut 21. During residual stress detection and surface defect detection with the linear welding, the sensor device 23 is placed parallel to the linear welding. In scanning the magnetic base 7 is adsorbed at the position of the linear welding 22, and the knob of the magnetic base 7 is rotated into "on" status, in order to keep the sensor device 23 firmly adsorbed on the detected region, and also keep the linear rail 20 parallel to the linear welding 22. During the internal defect detection with the linear welding, the sensor device 23 is placed perpendicular to the linear welding 22, of which both sides are provided with the sending transducer and receiving transducer. The running speed and running distance of the stepping motor can be controlled by software, and the scanning interval is setup. When the sensor device 23 arrives at the set position, the triggering signal is emitted by the grating scale, triggering the acquisition system to acquire the ultrasonic signal of the current position, and to process the relevant data, so that the automatic scanning can be achieved.

Linear welding automatic scanning device can realize automatic scanning process, adjust the scanning speed and ensure scanning at a constant speed. The scanned precise position information is recorded by the grafting scale, providing accurate estimation of the position of defect. By employment of the magnetic attraction technology, the sensor device 23 can be adsorbed in the region to be detected easily, and the magnetic base 7 can be turned on and off by artificial control. Installation of different sensor devices can allow, respectively, detection of welding residual stress, surface defect and welding internal defect for plate-like and curved-surface welding components, providing strong adaptability.

The configuration described in the above embodiments, is not used to limit the scope of protection of the claims in the present invention. A configuration described in one embodiment, without affecting its role, can be adapted to other embodiments. For example, in Embodiment 1 the threads can also be machined in the inclined plane of each plexiglass wedge 5, and the ultrasonic transducer can be attached to each plexiglass wedge 5 through threads, that is to say, through the same connecting method in Embodiment 2, and vice versa. The sonolucent wedge can also be made from other materials except plexiglass.

What is claimed is:

1. A sensor device, comprising:
two symmetrically disposed sonolucent wedges, and a connecting piece for fixedly connecting the two sonolucent wedges; the upper surface of each sonolucent wedge is provided with an inclined plane; an installation hole is formed on each inclined plane; each of transducers is installed in the respective installation hole, wherein one of the transducers is used to generate ultrasonic waves, and the other transducer is used to receive the ultrasonic waves generated by the previous transducer;
a circular boss projecting downward is formed at the bottom of each sonolucent wedge, the lower surface of the circular boss has the same curvature with the surface of the metal material to be measured.

2. The sensor device according to claim 1, wherein each installation hole is covered with a fixed plate of which the center is formed with a threaded hole, the fixed plate is fixed in each sonolucent wedge, each transducer is connected to the fixed plate through a thread.

3. The sensor device according to claim 1, wherein a magnetic base configured to fix the sensor device in the surface of the metal material to be measured, is mounted between two sonolucent wedges.

4. The sensor device according to claim 1, wherein a cavity is formed between the aperture wall of each installation hole and each transducer, in which a coupling agent is sealed.

5. The sensor device according to claim 4, wherein a small hole used for oiling into the cavity is perforated in the side wall of each sonolucent wedge.

6. A residual stress detection system, comprising a sensor device according to claim 1, an ultrasonic transmission card, and a data acquisition card; the ultrasonic waves generated by the ultrasonic transmission card is received by the sensor device and then collected by the data acquisition card.

7. The residual stress detection system according to claim 6, further comprising a temperature acquisition card configured to acquire real-time ambient temperature and eliminate the measurement error of stress due to change of ambient temperature.

8. The residual stress detection system according to claim 6, further comprising a calibration device configured to calibrate the incident angles of ultrasonic waves after simulating the curved surface with three-dimensional software during the detection of residual stress of the curved surface, so that the strongest waveform of excited $L_{CR}$ wave can be achieved.

9. The residual stress detection system according to claim 6, further comprising a stepping motor, a slider, a linear rail and a flexible strut, the sensor device is connected to the slider through the flexible strut, the slider is actuated by the stepping motor to move along the linear rail.

10. The residual stress detection system according to claim 9, wherein the stepping motor comprises a photoelectric encoder for recording and responding the position information of the sensor device.

11. The residual stress detection system according to claim 9, wherein the flexible strut provides constant pressure for the detection sensor, enabling a good coupling between the sensor device and the surface of the metal material to be measured.

12. The residual stress detection system according to claim 11, wherein the flexible strut includes a sleeve, a spring, a baffle, and a support piece, wherein the spring provides a pressing force to the flexible strut.

13. The residual stress detection system according to claim 6, further comprising a magnetic base configured to fix the sensor device in the surface of the metal material to be measured, mounted between two sonolucent wedges, and switched on and off through a knob, of which magnetic attraction force enables the sensor device to be firmly adsorbed on the metal material to be measured.

* * * * *